United States Patent [19]
Gonzenbach et al.

[11] Patent Number: 5,840,282
[45] Date of Patent: Nov. 24, 1998

[54] LIGHT SCREENING COMPOSITIONS

[75] Inventors: Hans Ulrich Gonzenbach, Geneva; Peter Gygax, Fällanden; Bernhard Hostettler; Ulrich Huber, both of Zürich, all of Switzerland

[73] Assignee: Givaudan-Roure (International) SA, Vernier-Geneva, Switzerland

[21] Appl. No.: 662,386

[22] Filed: Jun. 13, 1996

[30] Foreign Application Priority Data

Jun. 21, 1995 [EP] European Pat. Off. .............. 95810416

[51] Int. Cl.⁶ ................ A61K 7/42; A61K 7/44; A61K 7/00; A61K 31/135
[52] U.S. Cl. ................ 424/59; 424/60; 424/400; 424/401; 514/683
[58] Field of Search .................. 424/59, 60, 400, 424/401; 514/683

[56] References Cited

U.S. PATENT DOCUMENTS 4,387,089   6/1983   De Polo .

FOREIGN PATENT DOCUMENTS

| | | |
|---|---|---|
| 0 365 370 | 4/1990 | European Pat. Off. . |
| 0 474 063 | 3/1992 | European Pat. Off. . |
| 0 693 471 | 1/1996 | European Pat. Off. . |
| 2 636 531 | 12/1990 | France . |
| 29 27 820 | 1/1980 | Germany . |
| 37 41 420 | 6/1988 | Germany . |
| 38 33 706 | 4/1989 | Germany . |
| 642 536 | 4/1984 | Switzerland . |
| WO 93/16978 | 9/1993 | WIPO . |
| WO 94/04131 | 3/1994 | WIPO . |

OTHER PUBLICATIONS

Batouti, El. Chemical Abstracts, vol. 110, AN=74705.
Feuillerat, G. Chemical Abstracts, vol. 82, AN=85972.

*Primary Examiner*—Shelley A. Dodson
*Attorney, Agent, or Firm*—George W. Johnston; Alan P. Kass; Mark E. Waddell

[57] ABSTRACT

Photostable, cosmetic light-screening compositions for the protection of the human epidermis and the hairs against the ultraviolet rays of wavelengths between 320 and 400 nm, and between 320 and 400 nm respectively, comprising, in a cosmetically acceptable vehicle containing at least one fatty phase, about 0.75 to about 5%, in particular about 1 to about 4% by weight, of a dibenzoylmethane type UV-A screening agent and at least about 0.5% to about 2%, in particular about 0.5 to about 1% by weight, of a benzylidene type stabilizer of the general formula

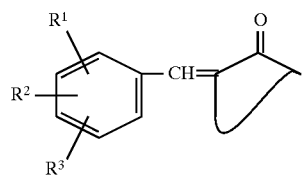

wherein

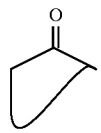

represents a bridged cyclic compound having the camphor (1,7,7-trimethyl-bicyclo[2.2.1]heptan-2-one), norcamphor (bicyclo[2.2.1]heptan-2-one), nopinone (6,6-dimethyl-bicyclo[3.1.1]heptan-2-one), pinocamphone (4,6,6-trimethyl-bicyclo[3.1.1]heptan-3-one), verbanone (4,6,6-trimethyl-bicyclo[3.1.1]heptan-2-one, thujone (1-isopropyl-4-methyl-bicyclo[3.1.0]hexan-3-one) or the 4,7-methano-octahydro-inden-5-one structure, and wherein $R^1$, $R^2$, $R^3$ independently signify hydrogen, lower alkyl, lower alkoxy, or 2 adjacent radicals represent methylene-dioxy, and where, in case of the camphor derivatives, the ratio of the UV-A filter to the stabilizer is greater than ca. 1.5:1, preferably ca. 2 to ca. 6:1, and where 4-methylbenzylidene camphor is excluded from the scope of formula I, and, optionally, at least one conventional UV-B filter.

13 Claims, No Drawings

LIGHT SCREENING COMPOSITIONS

FIELD OF THE INVENTION

The invention relates to photostable, cosmetic light-screening compositions for the protection of the human epidermis and the hairs against the ultraviolet rays of wavelengths between 320 and 400 nm, and between 320 and 400 nm respectively.

SUMMARY

The compositions comprise, in a cosmetically acceptable vehicle containing at least one fatty phase, about 0.75 to about 5%, in particular about 1 to about 4% by weight, of a dibenzoylmethane type UV-A screening agent and at least about 0.5 to about 2%, in particular about 0.5 to about 1% by weight, of a benzylidene type stabilizer of the general formula described below. Particular benzylidene type stabilizer compounds and processes for making them are also described herein.

DETAILED DESCRIPTION

The compositions of the invention comprise, in a cosmetically acceptable vehicle containing at least one fatty phase, about 0.75 to about 5%, in particular about 1 to about 4% by weight, of a dibenzoyl-methane type UV-A screening agent and at least about 0.5% to about 2%, in particular about 0,5 to about 1% by weight, of a benzylidene type stabilizer of the general formula

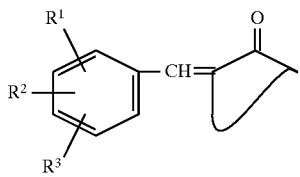

wherein

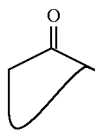

represents a bridged cyclic compound having a camphor (1,7,7-trimethyl-bicyclo [2.2.1]heptan-2-one), norcamphor (bicyclo[2.2.1]heptan-2-one), nopinone (6,6-dimethyl-bicyclo[3.1.1]heptan-2-one), pinocamphone (4,6,6-trimethyl-bicyclo[3.1.1]heptan-3-one), verbanone (4,6,6-trimethyl-bicyclo [3.1.1]heptan-2-one, thujone (1-isopropyl-4-methyl-bicyclo[3.1.0]hexan-3-one) or 4,7-methano-octahydro-inden-5-one structure, and wherein $R^1$, $R^2$, $R^3$ independently signify hydrogen, lower alkyl, lower alkoxy, or 2 adjacent radicals represent methylenedioxy, and where, in case of the camphor derivatives, the ratio of the UV-A filter to the stabilizer is greater than ca. 1.5:1, preferably ca. 2 to ca. 6:1, and where 4-methylbenzylidene camphor is excluded from the scope of formula I, and, optionally, at least one conventional UV-B filter.

The structures of these—as depicted ortho bound—formula II skeletons captioned above are as follows:

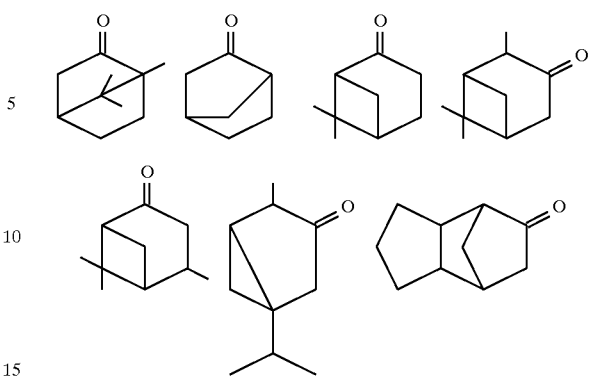

$R^1$, $R^2$ and $R^3$ preferably signify hydrogen or an alkyl group having up to 10, more preferably up to 8 carbon atoms. Particular examples include methyl, ethyl, propyl, isopropyl, n-butyl, secondary butyl, isobutyl, tert. butyl, n-pentyl, isopentyl, sec. pentyl, tert. pentyl, 2-methyl-butyl and neopentyl, hexyl, octyl, isooctyl, tert. octyl, etc.

Suitable alkoxy radicals are methoxy, ethoxy, propoxy, isopropoxy, etc. From this listing, it can also be deduced that the alkyl and the alkoxy radicals may in the present context represent straight-chain and branched radicals.

The preferred radicals are hydrogen, methyl, ethyl, propyl, isopropyl, t-butyl, methoxy, ethoxy, propoxy, isopropoxy. A further preferred aspect comprises compounds wherein $R^1$ and $R^2$ of (I) are hydrogen, or compounds wherein at least one R group of (I) is hydrogen, the other being hydrogen, methyl, isopropyl, t-butyl, methoxy or ethoxy.

Formula I should cover all possible stereoisomers, e.g. the diastereomers, the optical isomers, and the geometric, in particular the Z and E isomers as occurring at the α, β-unsaturated ketone moiety of the molecule.

Though the compounds I are themselves effective in absorbing the UV radiation, primarily in the erythemic region (290–320 nm), their present function is to photostabilize the above captioned UV-A-filters.

As far as the UV-A light screen agent of the novel combinations is concerned, the preferred compound is 4-tert. butyl-4'-methoxy-dibenzoylmethane, as disclosed e.g. in U.S. Pat. No. 4,387,089 or CH-Patent 642 536.

Other suitable dibenzoyl-methane derivative UV-A screening agents are: 2-methyl-dibenzoylmethane, 4-methyl-dibenzoyl-methane, 4-isopropyldibenzoyl-methane, 4-tert-butyldibenzoyl-methane, 2,4-dimethyl-dibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methodydibenzoylmethane.

The function of the formula I compound is, as pointed out above, to photostabilize the involved UV-A screening agents, i.e. to guarantee a constant protection during prolonged exposure to the UV light. This way, if a repeated application of the cosmetic formulation at various intervals is required, these intervals can be extended.

The present invention relates thus also to a process for stabilizing dibenzoylmethane UV-A screening agents with respect to the UV radiation of wavelengths between 320 and 400 nm, wherein about 0.5 to about 2% by weight of the stabilizer is added to 0.75 to 5% by weight of the dibenzoylmethane UV-A screening agent.

The desired stabilization of the material of UV-A filters is easily established by strictly parallel experiments with the respective UV-A filters and the novel compounds I using an appropriately equipped Xenon lamp as a solar simulator. Irradiation tests are conducted using standard preparations of the investigated products, e.g. solutions in, preferably, higher boiling cosmetic solvents, e.g. deltyl (isopropyl myristate), the resulting sunscreen being spread on glass plates. After the irradiation, the plates are immersed into a suitable solvent (e.g. ethanol) and the UV spectrum is recorded. The stabilizing effect is directly correlated to the difference in absorbance at $\lambda_{max}$ before and after the irradiation. Usually, a combination of 2% UV-A filter and 1% stabilizer is used for the assessment.

Both components of the present combination of the light-screening agents are lipophilic. The cosmetic formulations contain thus at least one fatty phase, and the formulations can consequently present themselves in the form of emulsions, lotions or gels.

Suitably the cosmetic screening composition takes the form of an oil, a lotion, a gel, a solid stick, an emulsion, e.g. cream, milk or of a vesicular dispersion of ionic or nonionic amphiphilic lipids, an aerosol, a spray, a foam, a powder, a shampoo, a hair conditioner or lacquer or a make-up, etc.

The usual solvents known to the skilled practitioner can be used for the preparation of these forms, e.g. oils, waxes, alcohols, polyols, etc. The preferred agents are fatty acids, esters, fatty alcohols, but also ethanol, isopropanol, propylene glycol, glycerine, etc.

The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments, etc.

UV-B filters may also be incorporated. Examples are given in U.S. Pat. No. 4,387,089 mentioned above. As still further suitable UV-B filters, microfine pigments, such as the usual micropigments of metal oxides may be used. Particularly in case of emulsions, such UV filters may, naturally, also be water-soluble derivatives. Suitable amounts of the UV-B filter are ca. 1–ca. 12%.

An important advantage of the novel stabilizer stems from the low dosage of the novel stabilizer—which dosage can be even considerably smaller than the dosages of the UV-A filter used—the practical user is thus completely free in the choice regarding the material used for the filtration of the UV-B rays.

In case of protection of the hairs, the suitable formulations are shampoos, conditioners, lotions, gels, emulsions, dispersions, lacquers, etc.

The preparation of all these formulations is well known to the skilled artisan in this field.

Examples of suitable stabilizers used for the present purpose are the ones of Table I below.

TABLE I

Illustrative Compounds

1)* 3-(4'-methoxy-benzylidene)-6,6-dimethyl-bicyclo[3.1.1]heptan-2-one;
2) 3-(benzylidene)-1,7,7-trimethyl-bicyclo[2.2.1]heptan-2-one;
3) 6-benzylidene-octahydro-4,7-methano-inden-5-one;
4) 3-benzylidene-4,6,6-trimethyl-bicyclo[3.1.1]heptan-2-one;
5) 3-(4'-methoxy-benzylidene)-1,7,7-trimethyl-bicyclo[2.2.1]heptan-2-one;
6) 3-(2'-methoxy-benzylidene)-1,7,7-trimethyl-bicyclo[2.2.1]heptan-2-one;

TABLE I-continued

Illustrative Compounds 7) 3-(2',3'-dimethoxy-benzylidene)-1,7,7-trimethyl-bicyclo[2.2.1]heptan-2-one;
8) 3-(3',5'-dimethoxy-benzylidene)-1,7,7-trimethyl-bicyclo[2.2.1]heptan-2-one;
9) 3-(3'-propoxy-benzylidene)-6,6-dimethyl-bicyclo[3.1.1]heptan-2-one;
10) 3-(2',4'-dimethyl-benzylidene)-1,7,7-trimethyl-bicyclo[2.2.1]heptan-2-one;
11) 2-(3'-methoxy-benzylidene)-1-isopropyl-4-methyl-bicyclo[3.1.0]hexan-3-one;
12) 3-(4'-tert.butyl-benzylidene)-6,6-dimethyl-bicyclo[3.1.1-heptan-2-one];
13)* 3-(3',4',5'-trimethoxy-benzylidene)-1,7,7-trimethyl-bicyclo[2.2.1]heptan-2-one;
14)* 3-(4'-tert.-butyl-benzylidene)-1,7,7-trimethyl-bicyclo[2.2.1]-heptan-2-one;
15)* 3-(4'-tert.-butyl-benzylidene)-bicyclo[2.2.1]heptan-2-one;
16) 6-(4'-tert.-butyl-benzylidne)-octahydro-4,7-methano-inden-5-one;
17)* 3-(4'-tert.-butyl-benzylidene)-4,6,6-trimethyl-bicyclo[3.1.1]heptan-2-one;
18)* 3-(4'-methoxy-benzylidene)-4,6,6-trimethyl-bicyclo[3.1.1]heptan-2-one;
19)* 2-(4'-tert.-butyl-benzylidene-4,6,6-trimethyl-bicyclo-[3.1.1]heptan-3-one;
20)* 6-(4'-methoxy-benzylidene)-octahydro-4,7-methano-inden-5-one;
21)* 2-(4'-methoxy-benzylidene)-4,6,6-trimethyl-bicyclo[3.1.1]heptan-3-one;
22) 3-(3',4'-methylenedioxy-benzylidene)-1,7,7-trimethyl-bicyclo[2.2.1] heptan-2-one;
23)* 3-(2'-methoxy-benzylidene)-bicyclo[2.2.1]heptan-2-one;
24*) 2-(2',4'-dimethyl-benzylidene)-4,6,6-trimethyl-bicyclo[3.1.1]heptan-3-one;
25) 6-(3',4'-dimethoxy-benzylidene)-4,7-methano-octahydro-inden-5-one;
26)* 6-(2'-methoxy-benzylidene)-4,7-methano-octahydro-inden-5-one.

The preferred compounds are Nos. 1, 5, 14, 16, 25 and 26.

Those compounds marked with a asterisk are novel compounds. The preparation of these novel compounds can be carried out using chemistry well-known to the skilled artisan. Thus a suitable process for the manufacture of the compounds I comprises subjecting the appropriate bi- or tricyclic compound II with the corresponding benzaldehyde to the conditions of an aldol condensation in basic medium, and encompassing a water separation, preferably at elevated temperatures, and separating the formed compound I from the reaction mixture.

The conditions of the aldol condensation between an aldehyde and a formula II keto compound having two active ortho hydrogens atoms are well-known to the skilled chemist.

The reaction partners are thus mixed, preferably in a ratio of ca. 1:ca. 1, in a suitable solvent. Such solvent is conveniently aprotic, e.g. is any ether or any optionally halogenated hydrocarbon, such as diethyl ether, benzene, toluene, or also dimethylformamide, etc. Crown ethers may be added as catalysts.

But also protic solvents, e.g. the usual aliphatic alcohols, such as methanol, ethanol or isopropanol are suitable. The reaction is preferably carried out at elevated temperatures, e.g. up to of the reflux temperature of the reaction mixture. But also ambient temperatures are suitable.

The reaction may be carried out in the presence of any strong base, e.g. any inorganic or organic such base, usually employed for the aldol condensation.

Suitable bases encompass thus in particular the (alkali) metal hydroxides, the alcoholates, the hydrides—and the (secondary) amines, such as pyrrolidine, morpholine, piperidine, etc.

EXAMPLES

1. The following three procedures A, B and C served to prepare the compounds I; the physical data were in each case in accordance with the postulated structure.

A. 10 g (65.7 mmoles) of camphor, 6,6 g of pulverized KOH and 2 g (7.5 mmoles) of 18-crown-6-ether were suspended under nitrogen in 180 ml of toluene. 12.9 g (65.7 mmoles) of 3,4,5-trimethoxy-benzaldehyde, dissolved in 50 ml of toluene were added. The mixture was heated to 70° C. for 18 hours. The reaction product was cooled and distributed between ether and water. The organic phases were dried with $Na_2SO_4$ and concentrated. The crude material was recrystallised from ether and a small amount of ethanol.

Yield: 13.2 g (61%) of white crystals of compound No. 13; mp 123° C., UV (EtOH): 313 nm (e=18319).

B. 10 g (65.7 mmoles) of camphor, 6,6 g of pulverized KOH and 2 g (7.5 mmoles) of 18-crown-6-ether were suspended under nitrogen in 180 ml of THF. 10.2 g (65.7 mmoles) of piperonal, dissolved in 50 ml of toluene were added. The mixture was heated to 65° C. for 18 hours. The reaction product was cooled and distributed between ether and water. The organic phases were dried with $Na_2SO_4$ and concentrated. The crude material was recrystallised from ether and a small amount of ethanol.

Yield: 13.7 g (74%) of white crystals of compound No. 22; mp 132° C., UV (EtOH): 333 nm (e=17545).

C. 21.8 g of potassium tert-butoxide were dissolved in 300 ml of tert-butanol. This mixture was added during 30 minutes to a well stirred solution of 22.8 g (±)-camphor and 40.8 g 2-methoxy benzaldehyde in 250 ml of tert-butanol. The reaction mixture was then stirred at room temperature for one day. The crude reaction product was transferred to a separation funnel, diluted with about 500 ml of tert-butyl-methyl ether, and washed with several portions of 10% sodium chloride in water. The organic layer was dried over magnesium sulfate, filtered and evaporated under reduced pressure. The crystalline faint yellow residue (51 g) was recrystallised from 25 ml of ethanol at 4° C. to give (after filtration and drying) 32.4 g (80% yield) of pure compound 6. UV (EtOH): 324 nm (e=12180).

2. Sunscreen lotions were prepared with the following ingredients:

Lotion a)

|   |   | % (w/w) |
|---|---|---|
| A | Glyceryl mono stearate | 4.0 |
|   | Octyl methoxycinnamate (PARSOL MCX ®) | 2.0 |
|   | Octyl salicylate | 2.0 |
|   | Butylmethoxy dibenzoylmethane (1-[4-(1,1-dimethylethyl)phenyl]-3-(4-methoxyphenyl)-1,3-propandione) (sold under the trade name PARSOL 1789 by Givaudan-Roure S.A.) | 2.0 |
|   | 3-(2'-Methoxy-benzylidene)-1,7,7-trimethyl-bicyclo[2.2.1]heptan-2-one | 0.5 |
|   | Cetyl alcohol | 1.0 |
|   | Coco-caprylate/caprate (Mixture of esters of coconut alcohol and n-octanoic acid and n-decanoic acid) (sold under the trade name CETIOL LC by Henkel) | 6.0 |
|   | Potassium cetyl phosphate (potassium salt of hexadecyl phosphate) (sold under the trade name AMPHISOL K by Givaudan-Roure S.A.) | 2.0 |
|   | EDTA $Na_2$ | 0.1 |
| B | Deionized water | 34.75 |
|   | Carbomer (1% dispersion in water, homopolymer of acrylic acid crosslinked with an allyl ether of sucrose) (sold under the trade name Carbopol 980 ® by B. F. Goodrich) | 10.0 |
|   | Propylene glycol | 5.0 |
|   | Potassium hydroxide, 10% solution | 0.45 |
|   | Mixture of parabens in phenoxy ethanol | 0.6 |
| C | Phenylbenzimidazole sulfonic acid | 2.0 |
|   | Deionized water | 20.0 |
|   | Potassium hydroxide, 10% solution | 3.6 |

Lotion b):

|   |   | % (w/w) |
|---|---|---|
| A | Glyceryl mono stearate | 4.0 |
|   | Octyl methoxycinnamate (PARSOL MCX ®) | 2.0 |
|   | Octyl salicylate | 2.0 |
|   | Butylmethoxy dibenzoylmethane (1-[4-(1,1-dimethylethyl)phenyl]-3-(4-methoxyphenyl)-1,3-propandione) (sold under the trade name PARSOL 1789 by Givaudan-Roure S.A.) | 2.0 |
|   | 3-(4'-Methoxy-benzylidene)-1,7,7-trimethyl-bicyclo[2.2.1]heptan-2-one | 0.5 |
|   | Cetyl alcohol | 1.0 |
|   | Coco-caprylate/caprate (Mixture of esters of coconut alcohol and n-octanoic acid and n-decanoic acid) (sold under the trade name CETIOL LC by Henkel) | 6.0 |
|   | Potassium cetyl phosphate (potassium salt of hexadecyl phosphate) (sold under the trade name AMPHISOL K by Givaudan-Roure S.A.) | 2.0 |
|   | EDTA $Na_2$ | 0.1 |
| B | Deionized water | 34.75 |
|   | Carbomer (1% dispersion in water, homopolymer of acrylic acid crosslinked with an allyl ether of sucrose) (sold under the trade name Carbopol 980 ® by B. F. Goodrich) | 10.0 |
|   | Propylene gylcol | 5.0 |
|   | Potassium hydroxide, 10% solution | 0.45 |
|   | Mixture of parabens in phenoxy ethanol | 0.6 |
| C | Phenylbenzimidazole sulfonic acid | 2.0 |
|   | Deionized water | 20.0 |
|   | Potassium hydroxide, 10% solution | 3.6 |

Lotion c):

|   |   | % (w/w) |
|---|---|---|
| A | Glyceryl mono stearate | 4.0 |
|   | Octyl diemthyl PABA (p-aminobenzoic acid) | 3.0 |
|   | Homosalate (Homomenthyl salicylate) | 1.0 |
|   | Benzophenone-3 | 2.0 |
|   | Butylmethoxy dibenzoylmethane | 2.0 |
|   | 3-(2'-Methoxy-benzylidene)-1,7,7-trimethyl-bicyclo[2.2.1]heptan-2-one | 0.5 |
|   | Cetyl alcohol | 1.0 |
|   | Coco-caprylate/caprate | 6.0 |
|   | Potassium cetyl phosphate (potassium salt of hexadecyl phospate) (sold under the trade name AMPHISOL K by Givaudan-Roure S.A.) | 2.0 |
|   | EDTA $Na_2$ | 0.1 |
| B | Deionized water | 62.16 |
|   | Carbomer (1% dispersion in water, homo- | 10.0 |

-continued

|   |   | % (w/w) |
|---|---|---|
|   | polymer of acrylic acid crosslinked with an allyl ether of sucrose) (sold under the trade name Carbopol 980 ® by B. F. Goodrich) |   |
|   | Propylene glycol | 5.0 |
|   | Potassium hydroxide, 10% solution | 0.64 |
|   | Mixture of parabens in phenoxyethanol | 0.6 |

Lotion d):

|   |   | % (w/w) |
|---|---|---|
| A | Glyceryl mono stearate | 4.0 |
|   | Octyl dimethyl PABA (p-aminobenzoic acid) | 3.0 |
|   | Homosalate (Homomenthyl salicylate) | 1.0 |
|   | Benzophenone-3 | 2.0 |
|   | Butylmethoxy dibenzoylmethane | 2.0 |
|   | 3-(4'-Methoxy-benzylidene)-1,7,7-trimethyl-bicyclo[2.2.1]heptan-2-one | 0.5 |
|   | Cetyl alcohol | 1.0 |
|   | Coco-caprylate/caprate | 6.0 |
|   | Potassium cetyl phosphate (potassium salt of hexadecyl phospate) (sold under the trade name AMPHISOL K by Givaudan-Roure S.A.) | 2.0 |
|   | EDTA Na$_2$ | 0.1 |
| B | Deionized water | 62.16 |
|   | Carbomer (1% dispersion in water, homo-polymer of acrylic acid crosslinked with an allyl ether of sucrose) (sold under the trade name Carbopol 980 ® by B. F. Goodrich) | 10.0 |
|   | Propylene glycol | 5.0 |
|   | Potassium hydroxide, 10% solution | 0.64 |
|   | Mixture of parabens in phenoxyethanol | 0.6 |

What is claimed is:

1. A photostable, cosmetic light-screening composition, comprising, in a cosmetically acceptable vehicle containing at least one fatty phase, about 0.75 to about 5% by weight, of a dibenzoylmethane derivative UV-A screening agent and at least about 0.5% to about 2% by weight, of a stabilizer of the general formula

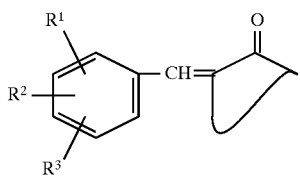

wherein

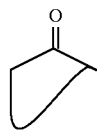

represents a bridged cyclic compound which is selected from the group consisting of camphor, norcamphor, nopinone, pinocamphone, verbanone, thujone, and 4,7-methano-octahydro-inden-5-one, and wherein $R^1$, $R^2$, $R^3$ independently signify hydrogen, lower alkyl, lower alkoxy, or 2 adjacent radicals represent methylenedioxy, and where, in case of the camphor derivatives, the ratio of the UV-A filter to the stabilizer is greater than about 1.5:1 and where 4-methylbenzylidene camphor is excluded from the scope of formula I.

2. The composition according to claim 1, wherein the UV-A-screening agent is present in amounts of ca. 1–ca. 4%, the stabilizer is present in amounts of ca. 0.5 to ca. 1%, and wherein the composition further includes a UV-B-filter which is present in amounts of ca. 1–ca. 12%.

3. The composition according to claim 1, wherein $R^1$, $R^2$ and $R^3$ of (I) are selected from hydrogen, methyl, ethyl, propyl, isopropyl, tert. butyl, methoxy, ethoxy, propoxy, and isopropoxy.

4. The composition according claim 1, wherein $R^1$ and $R^2$ of (I) are hydrogen.

5. The composition according to claim 1, wherein at least one of $R^1$, $R^2$ and $R^3$ is hydrogen, the others being hydrogen, methyl, isopropyl or tert. butyl, methoxy or ethoxy.

6. The composition according to claim 1, wherein the compound of formula I is 3-(4'-methoxy-benzylidene)-6,6-dimethyl-bicyclo[3.1.1]heptan-2-one;

3-(benzylidene)-1,7,7-trimethyl-bicyclo[2.2.1]heptane-2-one;

6-benzylidene-octahydro-4,7-methano-inden-5-one;

3-benzylidene-4,6,6-trimethyl-bicyclo[3.1.1]heptan-2-one;

3-(4'-methoxy-benzylidene)-1,7,7-trimethyl-bicyclo[2.2.1]heptan-2-one;

3-(2'-methoxy-benzylidene)-1,7,7-trimethyl-bicyclo[2.2.1]heptan-2-one;

3-(2',3'-dimethoxy-benzylidene)-1,7,7-trimethyl-bicyclo[2.2.1]heptan-2-one;

3-(3',5'-dimethoxy-benzylidene)-1,7,7-trimethyl-bicyclo[2.2.1]heptan-2-one;

3-(3'-propoxy-benzylidene)-6,6-dimethyl-bicyclo[3.1.1]heptan-2-one;

3-(2',4'-dimethyl-benzylidene)-1,7,7-trimethyl-bicyclo[2.2.1]heptan-2-one;

2-(3'-methoxy-benzylidene)-1-isopropyl-4-methyl-bicyclo[3.1.0]hexan-3-one;

3-(4'-tert.butyl-benzylidene)-6,6-dimethyl-bicyclo[3..1.1-heptan-2-one];

3-(4'-methoxy-benzylidene)-6,6-dimethyl-bicyclo [3.1.1] heptan-2-one;

3-(3',4',5'-trimethoxy-benzylidene)-1,7,7-trimethyl-bicyclo[2.2.1]heptan-2-one;

3-(4'-tert.-butyl-benzylidene)-1,7,7-trimethyl-bicyclo[2.2.1]-heptan-2-one;

3-(4'-tert.-butyl-benzylidene)-bicyclo[2.2.1]heptan-2-one;

6-(4'-tert.-butyl-benzylidene)-octahydro-4,7-methano-inden-5-one;

3-(4'-tert.-butyl-benzylidene)-4,6,6-trimethyl-bicyclo[3.1.1]heptan-2-one;

3-(4'-methoxy-benzylidene)-4,6,6-trimethyl-bicyclo[3.1.1]heptan-2-one;

2-(4'-tert.-butyl-benzylidene)-4,6,6-trimethyl-bicyclo-[3.1.1]heptan-3-one;

6-(4'-methoxy-benzylidene)-octahydro-4,7-methano-inden-5-one;

2-(4'-methoxy-benzylidene)-4,6,6-trimethyl-bicyclo[3.1.1]heptan-3-one;

3-(3',4'-methylene-dioxy benzylidene)1,7,7-trimethyl-bicyclo[2.2.1]heptan-2-one;

3-(2'-methoxy-benzylidene)-bicyclo [2.2.1]heptane-2-one;

2-(2',4'-dimethyl-benzylidene)-4,6,6-trimethyl-bicyclo[3.1.1]heptan-3-one;

6-(3',4'-dimethoxy-benzylidene)-4,7-methano-octahydro-indene-5-one or 6-(2'-methoxy-benzylidene)-4,7-methano-octahydro-inden-5-one.

7. The composition according to claim 1, wherein the compound of formula I is 3-(4'-methoxy-benzylidene)-6,6-dimethyl-bicyclo[3.1.1]heptan-2-one;

3-(4'-methoxy-benzylidene)-1,7,7-trimethyl-bicyclo[2.2.1]heptan-2-one;

3-(4'-tert.-butyl-benzylidene)-1,7,7-trimethyl-bicyclo[2.2.1]-heptan-2-one;

6-(4'-tert.-butyl-benzylidene)-octahydro-4,7-methano-inden-5-one;

6-(3',4'-dimethoxy-benzylidene)-4,7-methano-octahydro-indene-5-one or 6-(2'-methoxy-benzylidene)-4,7-methano-octahydro-inden-5-one.

8. The composition according to claim 1, wherein the dibenzoylmethane derivative UV screening agent is selected from the group consisting of 2-methyldibenzoylmethane, 4-methyl-dibenzoyl-methane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoyl-methane.

9. The composition according to claim 1, wherein the dibenzoylmethane derivative is 4-tert-butyl-4'-methoxydibenzoylmethane.

10. The composition according claim 1, which is an oil, a lotion, a gel, a solid stick, an emulsion, an aerosol, a spray, a foam, a powder, a shampoo, a hair conditioner or lacquer or a make-up.

11. The composition of claim 1, which further comprises one or more cosmetic adjuvants, selected from the group consisting of solvents, thickeners, emollients, emulsifiers, humectants, tensides, preservatives, antifoams, fragrances, oils, waxes, lower polyols and monohydric alcohols, propellants, silicones, colorings and pigments.

12. A method for the protection of the human epidermis or hairs against the damaging action of UV radiation of wavelengths between 290 and 400 nm, comprising applying to the skin or the hairs an effective amount of the cosmetic light-screening composition of claim 1.

13. A method for stabilizing dibenzoylmethane UV-A screening agents with respect to UV radiation of wavelengths between 320 and 400 nm, wherein ca. 0.5 to ca. 2% by weight of the stabilizer I defined in claim 1 is added to ca. 0.75 to ca. 5% by weight of the dibenzoylmethane UV-A light-screening agent.

* * * * *

UNITED STATES PATENT AND TRADEMARK OFFICE
CERTIFICATE OF CORRECTION

PATENT NO. : 5,840,282
DATED : November 24, 1998
INVENTOR(S) : HANS U. GONZENBACH et al It is certified that error appears in the above-identified patent and that said Letters Patent is hereby corrected as shown below:

Column 9, line 24:   Delete: "UV" and Insert: "UV-A"

Signed and Sealed this

Eighteenth Day of May, 1999

Attest:

Q. TODD DICKINSON

*Attesting Officer*    *Acting Commissioner of Patents and Trademarks*